US008698884B2

(12) United States Patent
Godo

(10) Patent No.: US 8,698,884 B2
(45) Date of Patent: Apr. 15, 2014

(54) LIGHT SOURCE APPARATUS

(71) Applicant: Olympus Medical System Corp., Tokyo (JP)

(72) Inventor: Hirokazu Godo, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/760,183

(22) Filed: Feb. 6, 2013

(65) Prior Publication Data
US 2013/0193875 A1    Aug. 1, 2013

Related U.S. Application Data

(63) Continuation of application No. PCT/JP2012/051819, filed on Jan. 27, 2012.

(30) Foreign Application Priority Data

Jan. 31, 2011    (JP) ................. 2011-018498

(51) Int. Cl.
H04N 7/18    (2006.01)

(52) U.S. Cl.
USPC ................. 348/68; 348/65; 348/71

(58) Field of Classification Search
USPC ............ 348/65, 70, 71, 68, 75, 79; 600/160, 600/178, 181, 476
See application file for complete search history.

(56) References Cited

U.S. PATENT DOCUMENTS 5,894,322 A * 4/1999 Hamano et al. ............. 348/68
5,910,816 A * 6/1999 Fontenot et al. ............ 348/65

(Continued)

FOREIGN PATENT DOCUMENTS

EP    1 804 108 A1    7/2007
JP    06-222287    8/1994

(Continued)

OTHER PUBLICATIONS

International Search Report dated Apr. 10, 2012 issued in PCT/JP2012/051819.

(Continued)

Primary Examiner — Tung X Le
(74) Attorney, Agent, or Firm — Scully, Scott, Murphy & Presser, P.C.

(57) ABSTRACT

A light source apparatus includes: a first light source unit including a plurality of light sources arranged therein, the plurality of light sources each emitting illuminating light in a first wavelength band; a second light source unit including a plurality of light sources arranged therein, the plurality of light sources each emitting illuminating light in a second wavelength band; an in-light source light guiding channel that guides the light emitted from the first light source unit and the light emitted from the second light source unit to a proximal end-side input end of a light guiding channel in an endoscope; and a light source control section that, based on endoscope information from an endoscope information storing section, divides the plurality of light sources in the first light source unit into a first light source group, light from which enters a vicinity of an optical axis of the proximal end-side input end of the light guiding channel in the endoscope, and a second light source group in a periphery of the first light source group, and divides the plurality of light sources in the second light source unit into a third light source group, light from which enters the vicinity of the optical axis of the proximal end-side input end of the light guiding channel in the endoscope, and a fourth light source group in a periphery of the third light source group, and performs control to decrease an output of the second light source group to be lower than an output of the first light source group and decrease an output of the fourth light source group to be lower than an output of the third light source group.

4 Claims, 9 Drawing Sheets

(56) References Cited

U.S. PATENT DOCUMENTS

| | | |
|---|---|---|
| 6,260,994 B1 | 7/2001 | Matsumoto et al. |
| 7,811,229 B2 * | 10/2010 | Sugimoto ..................... 600/160 |
| 8,040,373 B2 * | 10/2011 | Ayame et al. .................. 348/71 |
| 8,337,400 B2 * | 12/2012 | Mizuyoshi ..................... 600/178 |
| 2005/0265014 A1 | 12/2005 | Matsui et al. |
| 2008/0255411 A1 | 10/2008 | Kobayashi |

FOREIGN PATENT DOCUMENTS

| | | |
|---|---|---|
| JP | 2000-066115 | 3/2000 |
| JP | 2002-177218 | 6/2002 |
| JP | 2005-338280 | 12/2005 |
| JP | 2011-224044 | 11/2011 |

OTHER PUBLICATIONS

Extended Supplementary European Search Report dated Nov. 25, 2013 from related European Application No. 12 74 2658.3.

* cited by examiner

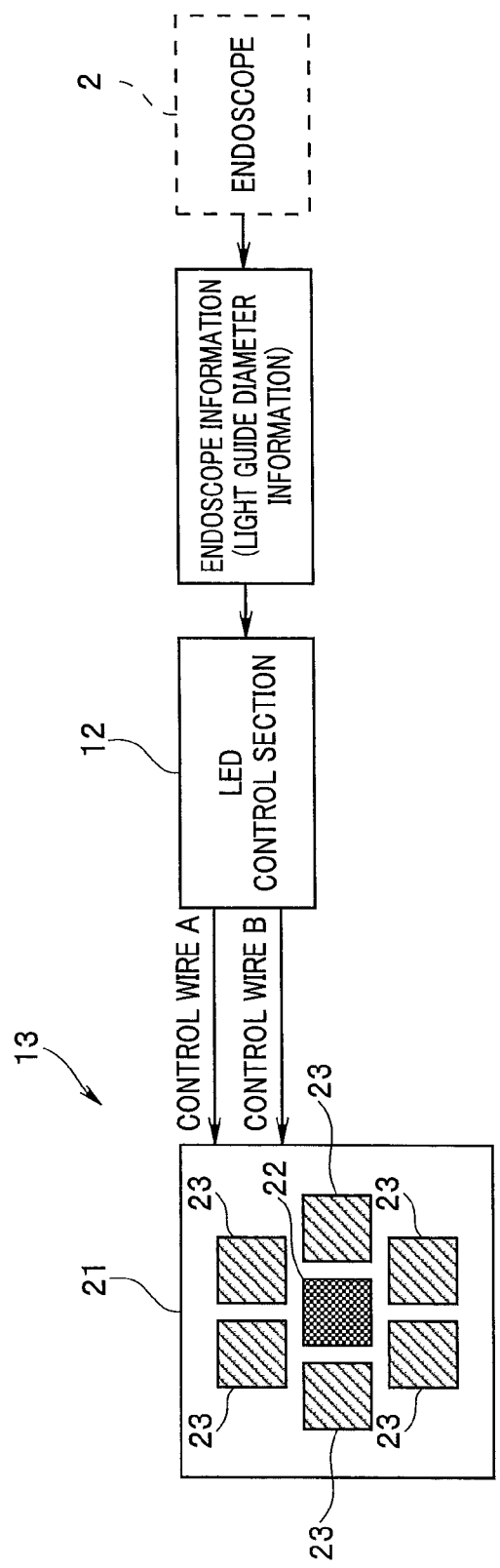

| | FIRST LIGHT SOURCE GROUP | | SECOND LIGHT SOURCE GROUP | |
|---|---|---|---|---|
| LIGHT ADJUSTMENT | CURRENT | DUTY RATIO | CURRENT | DUTY RATIO |
| 20% | 50% | 30% | 0% | 0% |
| 40% | 70% | 50% | 0% | 0% |
| 60% | 100% | 100% | 40% | 20% |
| 80% | 100% | 100% | 70% | 50% |
| 100% | 100% | 100% | 80% | 70% |

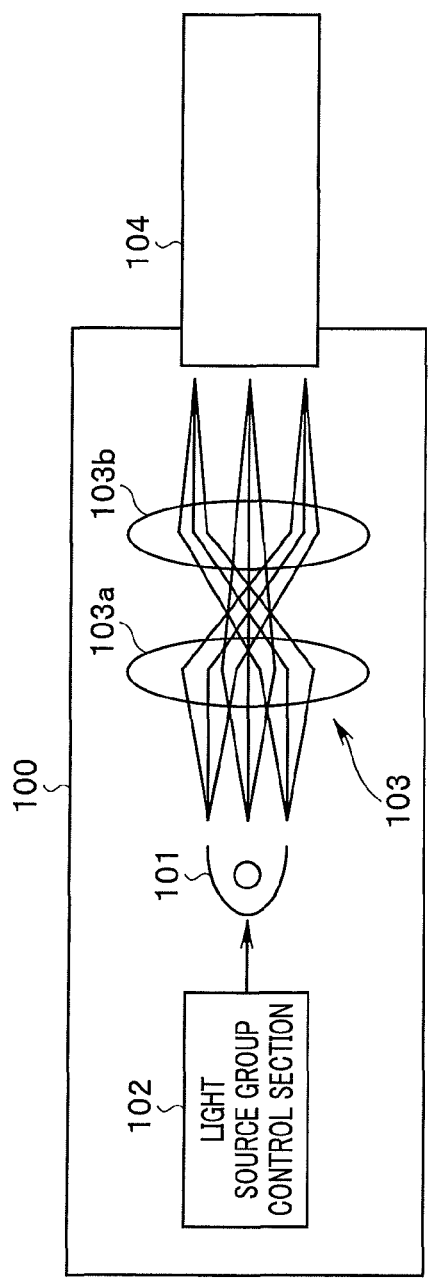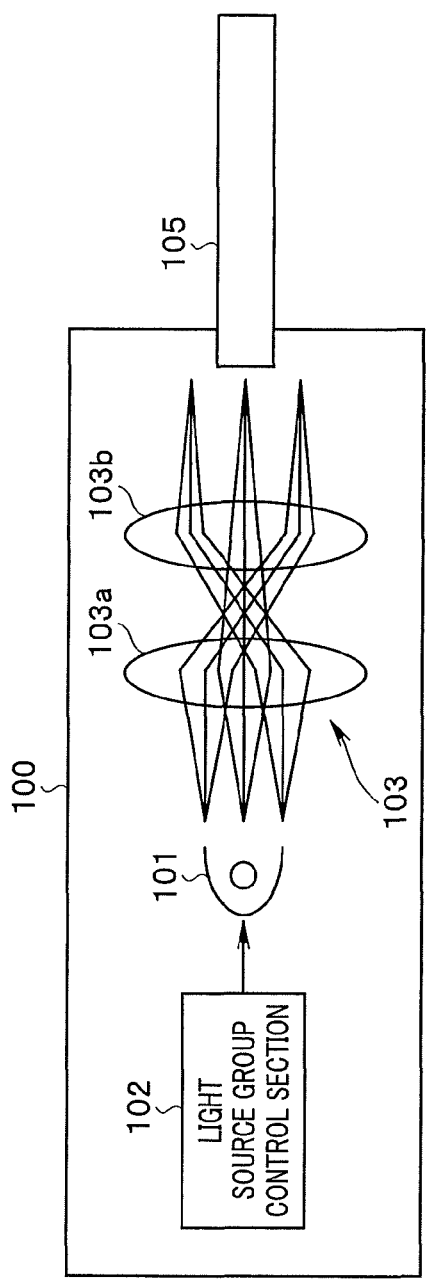
FIG.11A PRIOR ART
FIG.11B PRIOR ART

LIGHT SOURCE APPARATUS

CROSS REFERENCE TO RELATED APPLICATION

This application is a continuation application of PCT/JP2012/051819 filed on Jan. 27, 2012 and claims benefit of Japanese Application No. 2011-018498 filed in Japan on Jan. 31, 2011, the entire contents of which are incorporated herein by this reference.

BACKGROUND OF THE INVENTION

1. Field of the Invention

The present invention relates to a light source apparatus, and specifically relates to a light source apparatus that performs control of a light source based on endoscope information.

2. Description of the Related Art

Conventionally, when, e.g., an observation via an endoscope is performed, a light source apparatus that supplies illuminating light for illuminating a site to be examined to, e.g., a light guide provided in the endoscope is used. FIG. 11A is a diagram illustrating a configuration of a conventional light source apparatus where a large-diameter light guide is connected thereto, and FIG. 11B is a diagram illustrating a configuration of a conventional light source apparatus where a small-diameter light guide is connected thereto.

As illustrated in FIG. 11A, a conventional light source apparatus 100 includes a light source 101 such as a xenon lamp, a light source group control section 102 that performs turning-on control of the light source 101, and an optical system 103 including a plurality of lenses 103a and 103b, the optical system 103 collecting illuminating light from the light source 101. Such light source apparatus 100 is attachable/detachable to/from an endoscope, and a different type of endoscope is connected to the light source apparatus 100 depending on, e.g., the procedure, the observed site and/or the state of the patient.

In the example in FIG. 11A, an endoscope including a large-diameter light guide 104 is connected to the light source apparatus 100. The illuminating light from the light source 101, which has been collected by the optical system 103, enters an end face on the proximal end side of the large-diameter light guide 104.

On the other hand, as illustrated in FIG. 11B, where an endoscope including a small-diameter light guide 105 is connected to the light source apparatus 100, the illuminating light from the light source 101, which has been collected by the optical system 103, does not entirely enter an end face on the proximal end side of the small-diameter light guide 105.

Therefore, light source units for an electronic endoscope that when an electronic endoscope including a memory with information relating to a diameter size of a light guide recorded therein is connected thereto, reads the information relating to the diameter size of the light guide, and adjusts a position of the light source unit including a plurality of LEDs based on the read information have been proposed (see, for example, Japanese Patent Application Laid-Open Publication No. 2002-177218).

Such proposed light source units for an electronic endoscope each adjust the position of the light source unit relative to an entrance end of the light guide according to the diameter size of the light guide so that illuminating light efficiently enters the light guide.

SUMMARY OF THE INVENTION

A light source apparatus according to an aspect of the present invention provides a light source apparatus connectable to a proximal end-side input end of a light guiding channel in an endoscope, the endoscope including an endoscope information storing section that stores endoscope information, the light guiding channel that guides light from the proximal end side to a distal end side, and image pickup means for picking up an image of an object illuminated by illuminating light guided by the light guiding channel, the light source apparatus including: a first light source unit including a plurality of light sources arranged therein, the plurality of light sources each emitting illuminating light in a first wavelength band; a second light source unit including a plurality of light sources arranged therein, the plurality of light sources each emitting illuminating light in a second wavelength band; an in-light source light guiding channel that guides the light emitted from the first light source unit and the light emitted from the second light source unit to the proximal end-side input end of the light guiding channel in the endoscope; and a light source control section that, based on the endoscope information from the endoscope information storing section, divides the plurality of light sources in the first light source unit into a first light source group, light from which enters a vicinity of an optical axis of the proximal end-side input end of the light guiding channel in the endoscope, and a second light source group in a periphery of the first light source group, and divides the plurality of light sources in the second light source unit into a third light source group, light from which enters the vicinity of the optical axis of the proximal end-side input end of the light guiding channel in the endoscope, and a fourth light source group in a periphery of the third light source group, and performs control to decrease an output of the second light source group to be lower than an output of the first light source group and decrease an output of the fourth light source group to be lower than an output of the third light source group.

BRIEF DESCRIPTION OF THE DRAWINGS

FIG. 2 is a diagram for describing an example of a detailed configuration of a light source unit;

FIG. 11A is a diagram illustrating a configuration of a conventional light source apparatus where a large-diameter light guide is connected thereto; and FIG. 11B is a diagram illustrating a configuration of a conventional light source apparatus where a small-diameter light guide is connected thereto.

DETAILED DESCRIPTION OF THE PREFERRED EMBODIMENTS

Embodiments of the present invention will be described below with reference to the drawings.
(First Embodiment)

Figure 1:
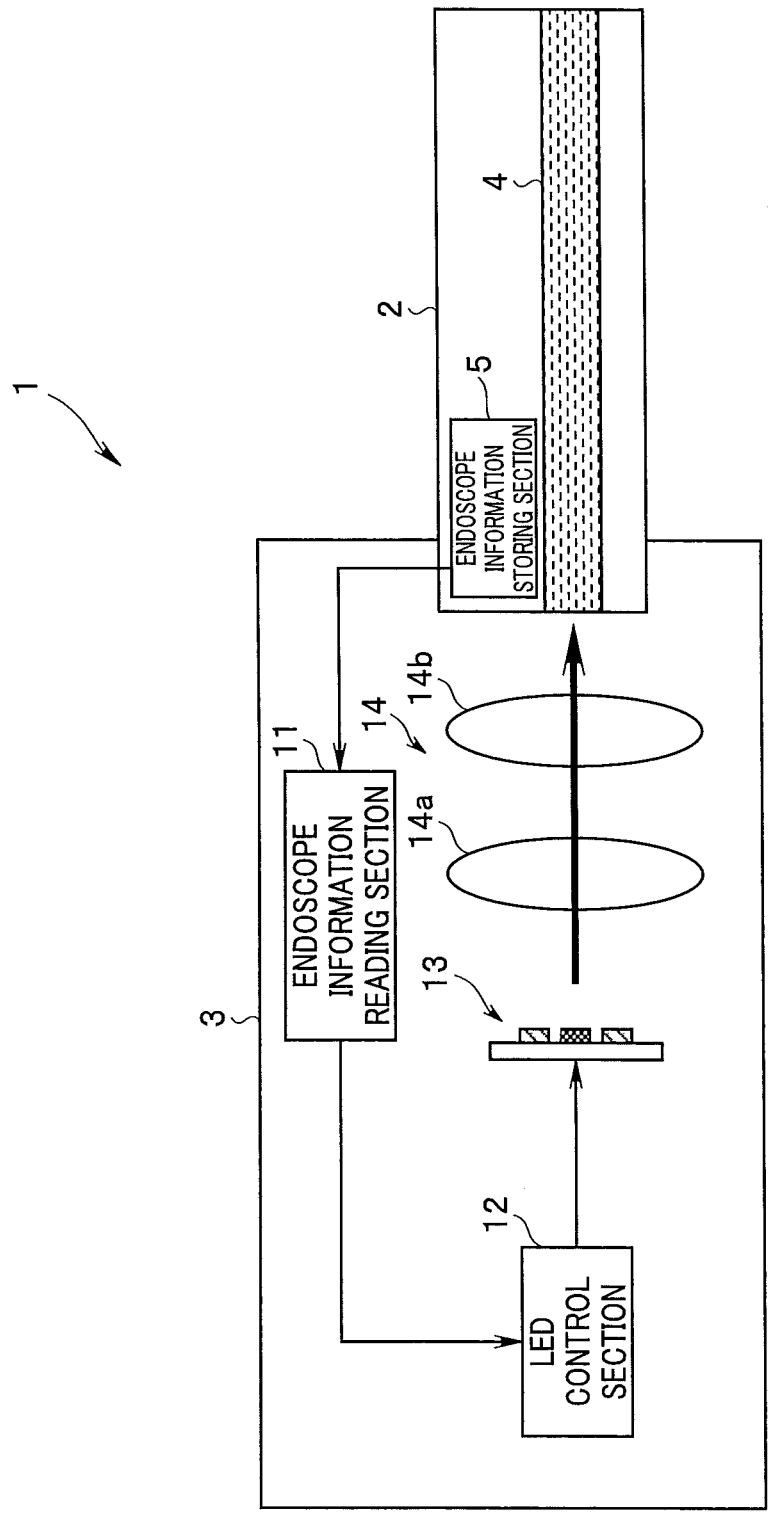
FIG. 1 is a diagram illustrating a configuration of an endoscope system including a light source apparatus according to a first embodiment.

FIG. 1 is a diagram illustrating a configuration of an endoscope system including a light source apparatus according to a first embodiment.

As illustrated in FIG. 1, an endoscope system 1 includes an endoscope 2 that picks up an image of an object inside a living body, and a light source apparatus 3 that supplies illuminating light for illuminating the object to the endoscope 2.

The endoscope 2 can be attached/detached to/from the light source apparatus 3 via, e.g., a non-illustrated connector. The endoscope 2 includes, in its inside, a light guide 4 inserted from the proximal end side to the distal end side, the light guide 4 guiding illuminating light from the light source apparatus 3, and an endoscope information storing section 5 with diameter information relating to a diameter size of the light guide 4 (hereinafter also referred to as "endoscope information") stored therein.

An end face on the light entrance side (hereinafter also referred to as "proximal end-side input end") of the light guide 4 is arranged on the proximal end side of the endoscope 2, and an end face on the light exit side (hereinafter also referred to as "distal end-side output end") of the light guide 4 is arranged on the distal end side of the endoscope 2. Where the endoscope 2 is connected to the light source apparatus 3, the proximal end-side input end of the light guide 4 is connected to the light source apparatus 3. The light guide 4, which serves as a light guiding channel, guides illuminating light inputted to the proximal end-side input end to the distal end-side output end. With such configuration as described above, illuminating light emitted from the light source apparatus 3 enters the proximal end-side input end and then exits from the distal end-side output end of the light guide 4, and illuminates an object inside a living body.

The light source apparatus 3 includes an endoscope information reading section 11, an LED control section 12, a light source unit 13 including a plurality of LEDs, and an optical system 14 including lenses 14a and 14b.

The endoscope information reading section 11 reads the endoscope information relating to the diameter size of the light guide 4 from the endoscope information storing section 5 in the endoscope 2 connected to the light source apparatus 3, and outputs the read endoscope information to the LED control section 12.

Note that, in the present embodiment, although the endoscope information storing section 5 with the endoscope information relating to the diameter size of the light guide 4 stored therein is provided in the endoscope 2, the endoscope information storing section 5 may be provided in the light source apparatus 3. In this case, information relating to types of endoscopes 2 (endoscope ID) and endoscope information relating to diameter sizes of light guides 4 are stored in a storage section in the light source apparatus 3 in association with each other. When an endoscope 2 is connected to the light source apparatus 3, the light source apparatus 3 reads information relating to the type of the connected endoscope 2 (endoscope ID) and outputs endoscope information relating to a diameter size of a corresponding light guide 4 to the LED control section 12.

The LED control section 12, which serves as a light source control section, performs control to turn on or off the LEDs, which serve as a plurality of light sources in the light source unit 13, based on the endoscope information inputted from the endoscope information reading section 11.

In the light source unit 13, the plurality of LEDs which emit illuminating light of a same color, that is, illuminating light in a same wavelength band are arranged. Note that details of an arrangement of the plurality of LEDs will be described with reference to FIG. 2. The plurality of LEDs in the light source unit 13 are turned on/off according to the control by the LED control section 12. Illuminating light from one or more LEDs turned on according to the control by the LED control section 12 enters the optical system 14.

The lenses 14a and 14b in the optical system 14 collect the illuminating light emitted from the light source unit 13 and makes the illuminating light enter the proximal end-side input end of the light guide 4. As described above, the optical system 14 provides an in-light source light guiding channel that guides light emitted from the light source unit 13 to the proximal end-side input end of the light guide 4 in the endoscope 2. The illuminating light that has entered the proximal end-side input end of the light guide 4 exits from the distal end-side output end and illuminates an object.

Here, a detailed configuration of the light source unit 13 in the light source apparatus 3 configured as described above and a lighting state of the light source unit 13 will be described.

Figure 3A:
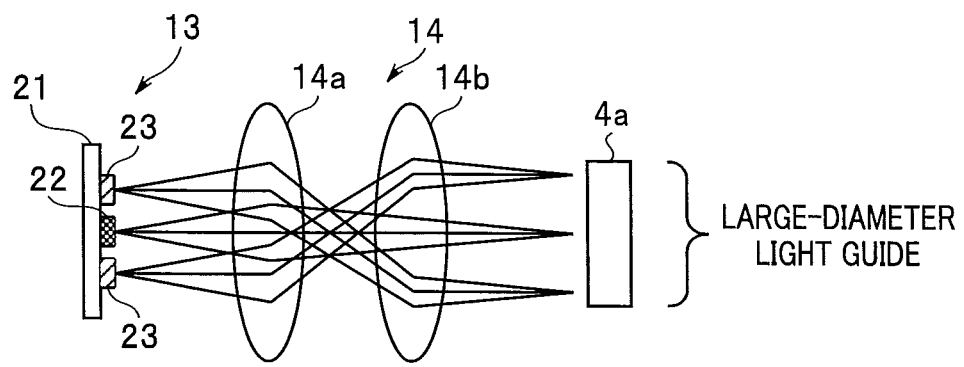
FIG. 3A is a diagram for describing an example of a lighting state of a light source unit where a large-diameter light guide is connected thereto.
Figure 3B:
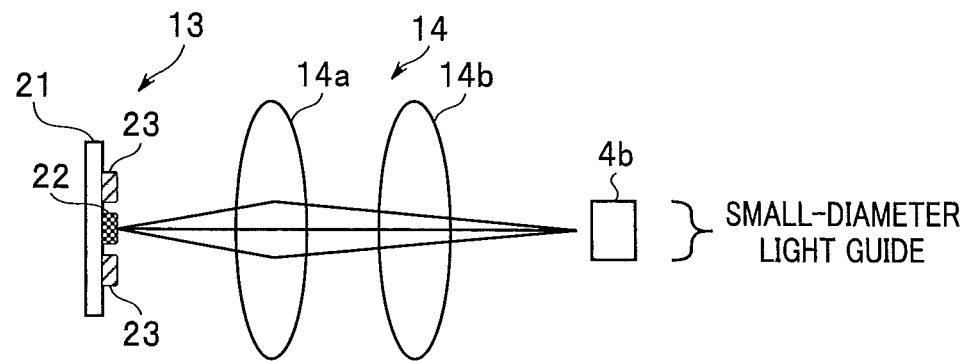
FIG. 3B is a diagram for describing an example of a lighting state of a light source unit where a small-diameter light guide is connected thereto.

FIG. 2 is a diagram for describing an example of a detailed configuration of a light source unit, FIG. 3A is a diagram for describing an example of a lighting state of a light source unit where a large-diameter light guide is connected thereto, and FIG. 3B is a diagram for describing an example of a lighting state of a light source unit where a small-diameter light guide is connected thereto.

As illustrated in FIG. 2, the light source unit 13 includes an LED substrate 21, and a plurality of LEDs 22 and 23 arranged on the LED substrate 21. The LED 22, which serves as a first light source group, is arranged in a substantial center of the LED substrate 21, and the LEDs 23, which serve as a second light source group, include six LEDs 23, and are arranged on the LED substrate 21 substantially annularly with the LED 22 as a center.

Illuminating light from the LED 22, which serves as the first light source group, enters a vicinity of an optical axis (center axis) of the proximal end-side input end of the light guide 4. Illuminating light from the LEDs 23, which serve as the second light source group arranged in the periphery of the first light source group, enters a periphery of the optical axis (center axis) of the proximal end-side input end of the light guide 4 relative to the illuminating light from the LED 22. Note that, although the first light source group includes one LED 22, the first light source group may include two or more LEDs. Therefore, although only one LED 22 is provided here, the LED 22 is referred to as "first light source group".

The LED control section 12 is connected to the light source unit 13 via two control wires, i.e., a control wire A and a control wire B. For example, the control wire A is a control wire for controlling turning-on or off of the LED 22, which serves as the first light source group, and the control wire B is a control wire for controlling turning-on or off of the LEDs 23, which serve as the second light source group.

The LED control section 12 performs control to turn on or off the LED 22, which serves as the first light source group, and the LEDs 23, which serve as the second light source group, via the control wire A and the control wire B based on the endoscope information read from the endoscope 2.

Where a large-diameter light guide 4a is connected as illustrated in FIG. 3A, the LED control section 12 performs control to turn on the LED 22, which serves as the first light source group, and the LEDs 23, which serve as the second light source group. On the other hand, where a small-diameter light guide 4b is connected as illustrated in FIG. 3B, the LED control section 12 performs control to turn on the LED 22, which serves as the first light source group, and turn off the LEDs 23, which serve as the second light source group, arranged in the periphery of the first light source group.

As described above, where it is determined based on endoscope information read from the endoscope information storing section 5 that the small-diameter light guide 4b is connected, the LED control section 12 performs control to stop an output of the LEDs 23, which serve as the second light source group. Note that, where it is determined that the small-diameter light guide 4b is connected, the LED control section 12 may perform control to decrease the output of the LEDs 23, which serves as the second light source group, to be lower than an output of the first light source group.

As described above, the light source apparatus 3 is configured to control to turn on or off the LED 22, which serves as the first light source group, and the LEDs 23, which serve as the second light source group, based on endoscope information relating to a diameter size of a light guide 4 in an endoscope 2 connected thereto. Consequently, the number of LEDs turned on according to the diameter size of the light guide 4 can be controlled, that is, the control to turn on the first light source group and the control to turn on the second light source group can be performed individually, enabling suppression of wasted light generation and temperature increase.

Accordingly, a light source apparatus according to the present embodiment enables reduction of noise of a cooling fan due to heat generation.

(Second Embodiment)

Next, a second embodiment will be described.

Figure 4:
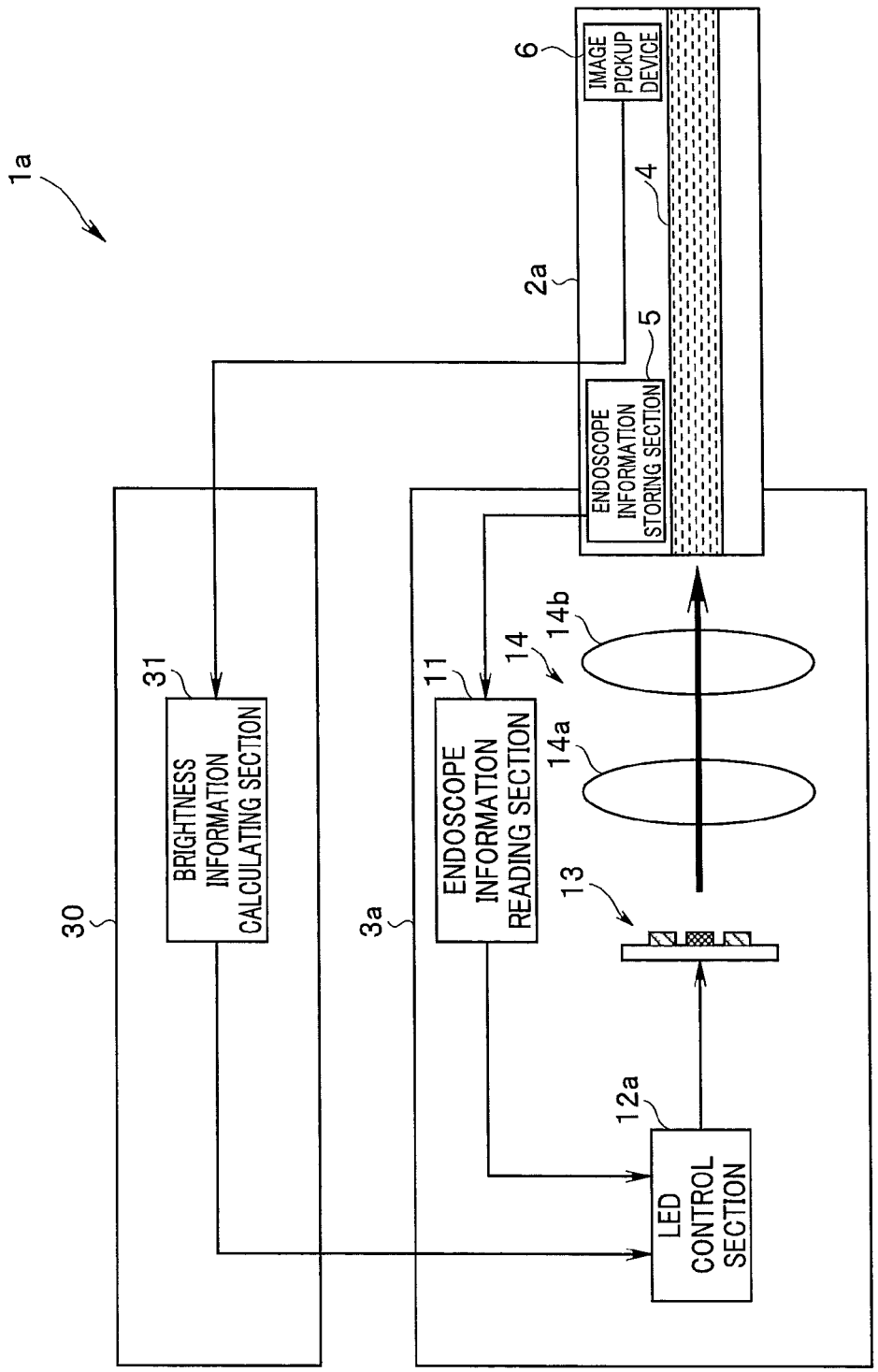
FIG. 4 is a diagram illustrating a configuration of an endoscope system including a light source apparatus according to a second embodiment.

FIG. 4 is a diagram illustrating a configuration of an endoscope system including a light source apparatus according to a second embodiment. Note that in FIG. 4, components that are the same as those in FIG. 1 are provided with reference numerals that are the same as those in FIG. 1, and a description thereof will be omitted.

As illustrated in FIG. 4, an endoscope system 1a includes an endoscope 2a, a light source apparatus 3a and a processor 30.

At a distal end of the endoscope 2a, a non-illustrated objective lens for forming an optical image of an illuminated object is provided. At a position where an image is formed via the objective lens, an image pickup device 6 such as a CCD is provided. The image pickup device 6 photoelectrically converts the formed optical image to generate an image pickup signal. The image pickup device 6 is connected to a processor 30 via a signal wire, and outputs the generated image pickup signal to the processor 30 via the signal wire.

The processor 30 includes a brightness information calculating section 31, and the image pickup signal from the image pickup device 6 is supplied to the brightness information calculating section 31.

The brightness information calculating section 31 calculates brightness information on the picked-up image from the image pickup signal supplied from the image pickup device 6. Note that the brightness information is not limited to picked-up image information and may be, for example, numerical value data of luminance information. The brightness information calculating section 31 outputs the calculated brightness information to an LED control section 12a in the light source apparatus 3a.

The LED control section 12a performs control to turn on or off an LED 22, which serves as a first light source group, and LEDs 23, which serve as a second light source group, as well as light adjustment control for the LED 22 and the LEDs 23, based on endoscope information from an endoscope information reading section 11 and the brightness information from the brightness information calculating section 31. The rest of the configuration is similar to that of the first embodiment.

Here, a detailed configuration of a light source unit 13 in the light source apparatus 3a configured as described above and a lighting state and light adjustment control for the light source unit 13 will be described.

Figure 5:
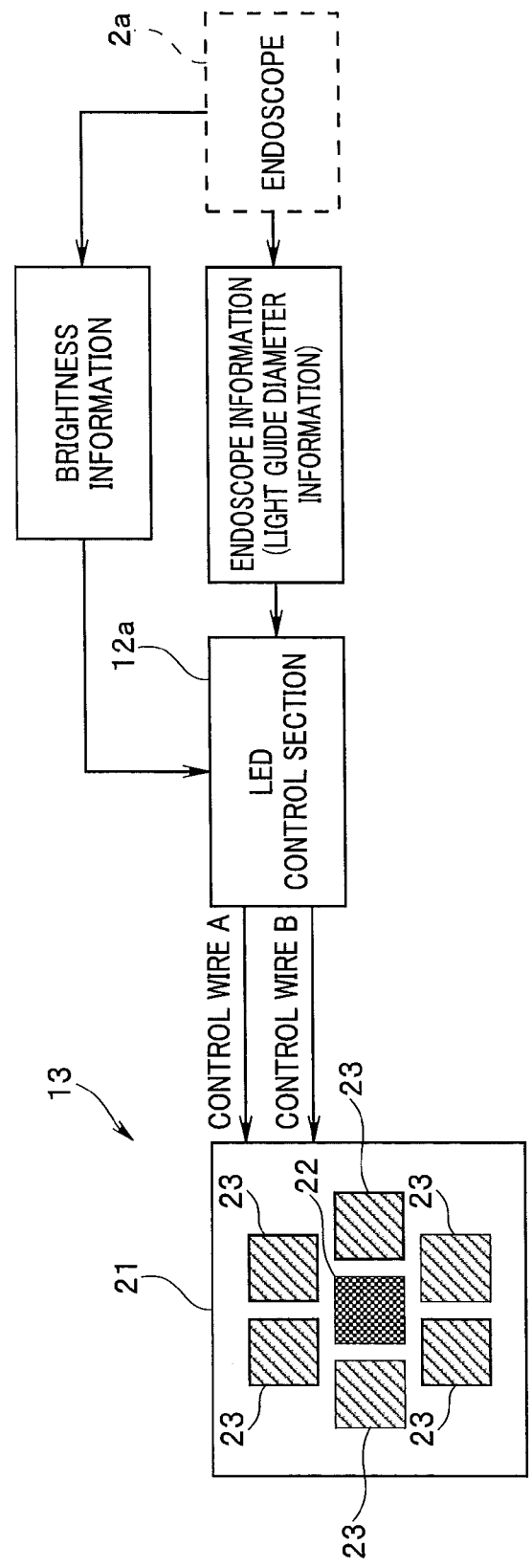
FIG. 5 is a diagram for describing an example configuration of a detailed configuration of a light source unit.
Figures 6, 7:
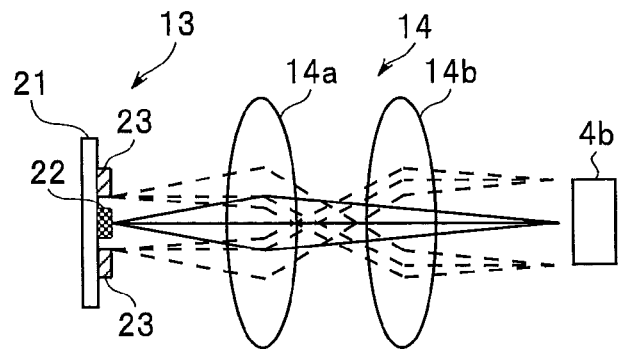
FIG. 6 is a diagram for describing an example of a lighting state of a light source unit.
FIG. 7 is a diagram for describing an example of light adjustment control by a light source unit.

FIG. 5 is a diagram for describing an example of a detailed configuration of a light source unit, FIG. 6 is a diagram for describing an example of a lighting state of a light source unit, and FIG. 7 is a diagram illustrating an example of light adjustment control by a light source unit.

As illustrated in FIG. 5, a configuration of the light source unit 13 is similar to that of the first embodiment. In the present embodiment, in addition to endoscope information, brightness information is inputted to the LED control section 12a, which serves as brightness information input means. Brightness information is information calculated from an image pickup signal obtained by the image pickup device 6 in the endoscope 2a, which has been supplied to the brightness information calculating section 31 in the processor 30.

The LED control section 12a performs control to turn on or off the LED 22, which serves as the first light source group, and the LEDs 23, which serve as the second light source group, and light adjustment control for the LED 22 and the LEDs 23, based on the inputted endoscope information and brightness information.

As illustrated in FIG. 6, in the case of the LEDs 23, which serve as the second light source group arranged in the periphery of the LED 22, which serves as the first light source group, also, illuminating light generated at a position close to a center of an LED substrate 12 enters a proximal end-side input end of a small-diameter light guide 4b. Accordingly, the LED control section 12a performs light adjustment control for the LED 22 (first light source group) and the LEDs 23 (second light source group) according to a light adjustment ratio calculated based on brightness information. In particular, the LED control section 12a controls a current value and a pulse width (duty ratio) of each of the current supplied to the LED 22 (first light source group) and the current supplied to the LEDs 23 (second light source group), according to the light adjustment ratio.

As illustrated in FIG. 7, the LED control section 12a controls the current value and the duty ratio of each of the current supplied to the LED 22 (first light source group) and the current supplied to the LEDs 23 (second light source group) based on brightness information. For example, in the case of a light adjustment ratio of 20%, the LED control section 12a controls the current value of the current supplied to the LED 22 (first light source group) to 50% and controls the duty ratio of the same to 30%, and controls the current value of the current supplied to the LEDs 23 (second light source group) to 0% and the duty ratio of the same to 0%. Also, for example, in the case of a light adjustment ratio of 100%, the LED control section 12a controls the current value of the current supplied to the LED 22 (first light source group) to 100% and the duty ratio of the same to 100%, and the current value of the current supplied to the LEDs 23 (second light source group) to 80% and the duty ratio of the same to 70%.

As described above, when the LED control section 12a reduces illuminating light emitted from the light source unit 13 based on brightness information, the LED control section 12a performs control to decrease an output of the LEDs 23, which serve as the second light source group, in preference to the LED 22, which is the first light source group.

As described above, the light source apparatus 3a according to the present embodiment is configured to perform turning-on and light adjustment control for the first light source group and the second light source group based on brightness information in addition to endoscope information relating to a diameter size of a light guide 4. Consequently, the lighting and light adjustment control for the first light source group and the lighting and light adjustment control for the second light source group can be performed individually, enabling suppression of wasted light generation and temperature increase.

Accordingly, as with the first embodiment, a light source apparatus according to the present embodiment enables reduction of noise of a cooling fan due to heat generation.

(Modification)

Light source apparatuses according to embodiments of the present invention are not limited to the light source apparatuses 3 and 3a according to the above-described first and second embodiments. For example, it is not necessary that an arrangement of an LED 22, which serves as a first light source group, and LEDs 23, which serve as a second light source group, be the arrangement in FIG. 2.

Figure 8A:
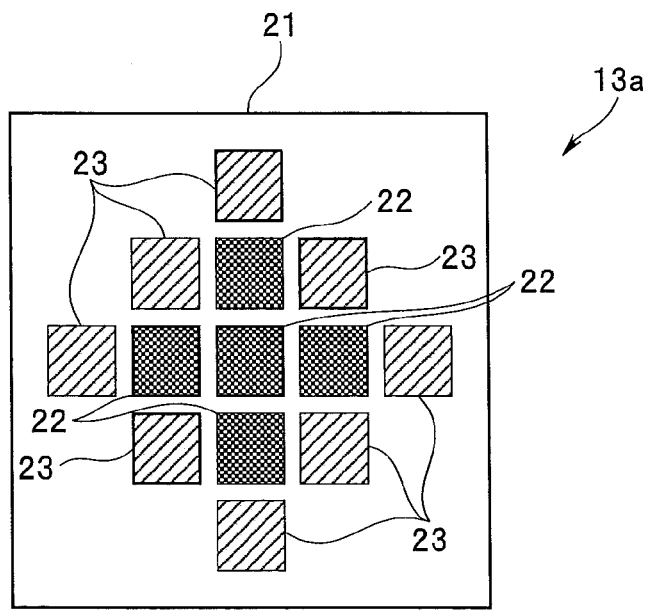
FIG. 8A is a diagram for describing an example of another arrangement of LEDs.
Figure 8B:
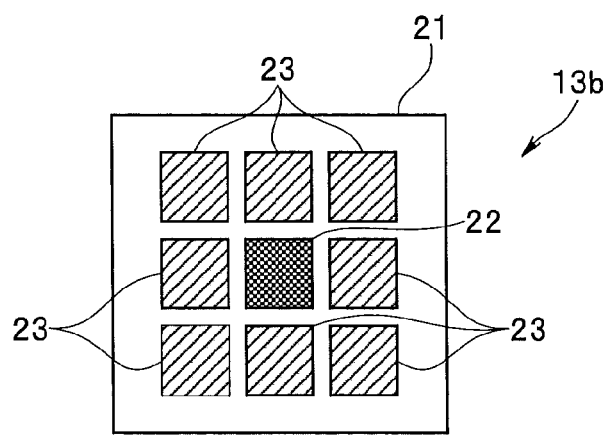
FIG. 8B is a diagram for describing an example of another arrangement of LEDs.
Figure 8C:
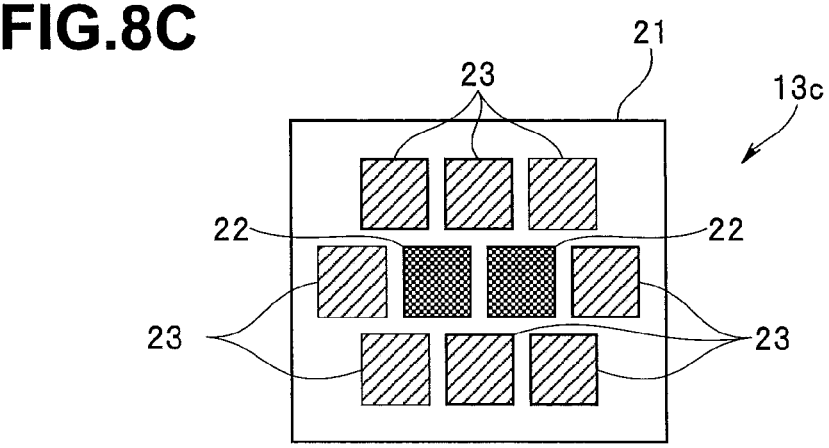
FIG. 8C is a diagram for describing an example of another arrangement of LEDs.

FIGS. 8A, 8B and 8C are diagrams each illustrating an example of another arrangement of LEDs.

A light source unit 13a, which is illustrated in FIG. 8A, includes five LEDs 22, which serve as a first light source group arranged in a substantial center of an LED substrate 21 and above, below and on the left and right of the substantial center, and eight LEDs 23, which serve as a second light source group arranged in a substantially rhombic shape in the periphery of the first light source group.

A light source unit 13b, which is illustrated in FIG. 8B, includes one LED 22, which serves as a first light source group arranged at a substantial center of an LED substrate 21, and eight LEDs 23, which serve as a second light source group arranged in a substantially quadrangular shape in the periphery of the first light source group.

A light source unit 13, which is illustrated in FIG. 8C, includes two LEDs 22, which serve as a first light source group arranged on the left and right of a substantial center of an LED substrate 21, and eight LEDs 23, which serve as a second light source group arranged in a substantially oval shape in the periphery of the first light source group.

As described above, the first and second light source group arrangement is not limited to the first and second light source group arrangement illustrated in FIG. 2.

Also, although the light source units 13 according to the first and second embodiments each have a configuration including an LED 22, which serves as a first light source group, and LEDs 23, which serve as a second light source group, a configuration including three or more light source groups may be employed.

Figure 9:
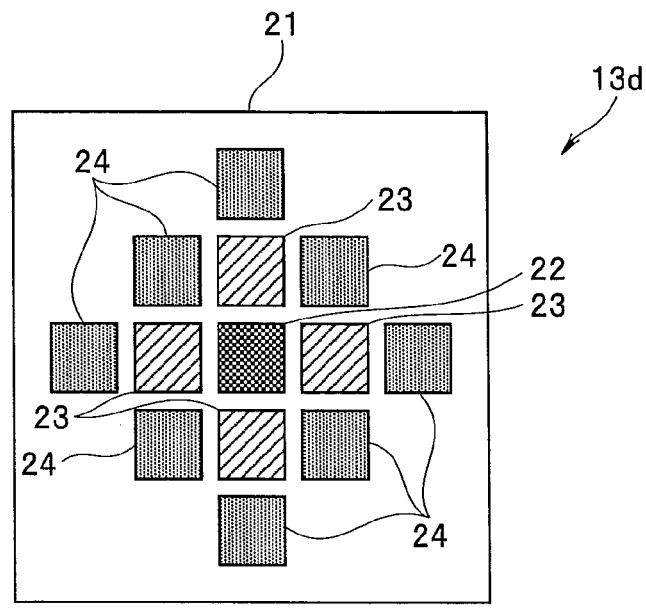
FIG. 9 is a diagram for describing an example of a light source unit including three light source groups.

FIG. 9 is a diagram illustrating an example of a light source unit including three light source groups.

As illustrated in FIG. 9, an arrangement of LEDs in a light source unit 13d is similar to that in FIG. 8A.

The light source unit 13d includes one LED 22, which serves as a first light source group arranged in a substantial center of an LED substrate 21, four LEDs 23, which serve as a second light source group arranged above, below and on the left and right of the first light source group, and eight LEDs 24, which serve as a third light source group arranged in a substantially rhombic shape in the periphery of the second light source group.

In such light source unit 13d including three light source groups (in one including three or more light source groups as well), the first light source group, the second light source group and the third light source group are arranged in this order from a center of an optical axis, in other words, a center of the LED substrate 21. Also, where control for three light source groups is performed, a control wire C is provided between the LED control section 12 and the light source unit 13 in addition to the control wire A and the control wire B described above, control to turn on and off the LEDs 24, which serve as the third light source group, is performed using the control wire C.

Furthermore, although the light source apparatuses 3 according to the first and second embodiments each have a configuration including one light source unit 13, a configuration including two or more light source units may be employed.

Figure 10:
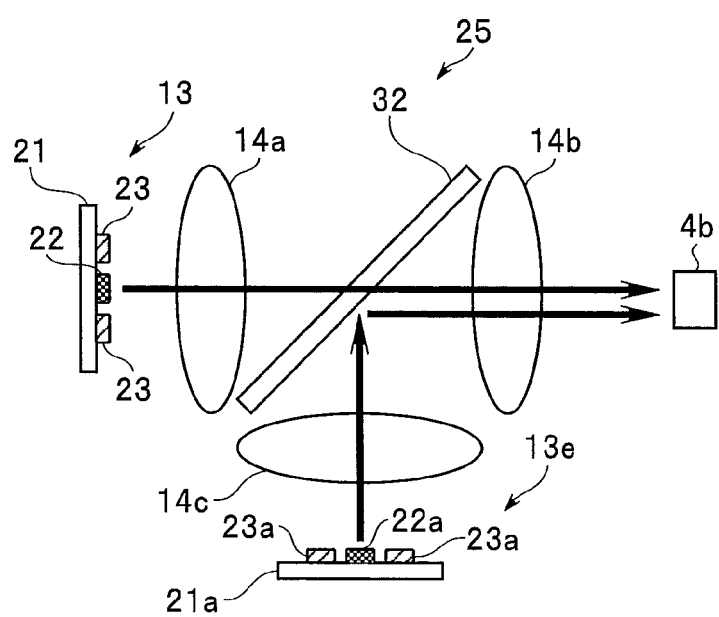
FIG. 10 is a diagram for describing an example of a light source apparatus including a plurality of light source units.

FIG. 10 is a diagram for describing an example of a light source apparatus including a plurality of light source units.

As illustrated in FIG. 10, a light source apparatus 3 includes a light source unit 13e in addition to a light source unit 13. The light source unit 13e, which has a configuration similar to that of the light source unit 13, includes an LED 22a, which serves as a first light source group, and LEDs 23a which serve as a second light source group, on an LED substrate 21a. Although these LED 22a and LEDs 23a emit illuminating light in a same wavelength band, an LED 22a and LEDs 23a emit illuminating light in different wavelength bands from those of LED 22 and LED 23.

Also, an optical system 14 includes a lens 14c that collects illuminating light from the light source unit 13e and a dichroic filter 32 that combines an optical path of illuminating light from the light source unit 13 and an optical path of illuminating light from the light source unit 13e, in addition to lenses 14a and 14b.

The dichroic filter 32 transmits illuminating light emitted from the light source unit 13 and reflects illuminating light emitted from the light source unit 13e, whereby the optical path of the illuminating light from the light source unit 13 and the optical path of the illuminating light from the light source unit 13e are combined.

As described above, where a plurality of light source units 13 and 13e are provided, it is only necessary to change a relevant optical path using, e.g., a dichroic filter 32.

The present invention is not limited to the above-described embodiments and modification, and various variations, alterations and the like are possible without departing from the spirit of the present invention.

What is claimed is:

1. A light source apparatus connectable to a proximal end-side input end of a light guiding channel in an endoscope, the endoscope including an endoscope information storing section that stores endoscope information, the light guiding channel that guides light from the proximal end side to a distal end side, and image pickup means for picking up an image of an object illuminated by illuminating light guided by the light guiding channel, the light source apparatus comprising:

a first light source unit including a plurality of light sources arranged therein, the plurality of light sources each emitting illuminating light in a first wavelength band;

a second light source unit including a plurality of light sources arranged therein, the plurality of light sources each emitting illuminating light in a second wavelength band;

an in-light source light guiding channel that guides the light emitted from the first light source unit and the light emitted from the second light source unit to the proximal end-side input end of the light guiding channel in the endoscope; and a light source control section that, based on the endoscope information from the endoscope information storing section, divides the plurality of light sources in the first light source unit into a first light source group, light from which enters a vicinity of an optical axis of the proximal end-side input end of the light guiding channel in the endoscope, and a second light source group in a periphery of the first light source group, and divides the plurality of light sources in the second light source unit into a third light source group, light from which enters the vicinity of the optical axis of the proximal end-side input end of the light guiding channel in the endoscope, and a fourth light source group in a periphery of the third light source group, and performs control to decrease an output of the second light source group to be lower than an output of the first light source group and decrease an output of the fourth light source group to be lower than an output of the third light source group.

2. The light source apparatus according to claim 1, wherein the light source control section performs control to stop the output of the second light source group and stop the output of the fourth light source group.

3. The light source apparatus according to claim 1, further comprising brightness information input means for inputting brightness information on a picked-up image picked up by the image pickup means in the endoscope, wherein when the light source control section performs control to reduce the light emitted from each of the light source units based on the brightness information, the light source control section performs control to decrease the output of the second light source group in preference to the first light source group and decrease the output of the fourth light source group in preference to the third light source group.

4. The light source apparatus according to claim 1, wherein the plurality of light sources in the light source units are LEDs.

* * * * *